United States Patent
Doan

(10) Patent No.: US 8,747,819 B1
(45) Date of Patent: Jun. 10, 2014

(54) NAIL ENAMEL COMPOSITION, METHOD OF PREPARATION AND METHOD OF USE

(71) Applicant: Amy Doan, Garden City, CA (US)

(72) Inventor: Amy Doan, Garden City, CA (US)

( * ) Notice: Subject to any disclaimer, the term of this patent is extended or adjusted under 35 U.S.C. 154(b) by 0 days.

(21) Appl. No.: 13/776,269

(22) Filed: Feb. 25, 2013

Related U.S. Application Data

(62) Division of application No. 13/633,439, filed on Oct. 2, 2012.

(51) Int. Cl.
*A61K 8/40* (2006.01)
*A61Q 3/02* (2006.01)

(52) U.S. Cl.
USPC .............................................. 424/61

(58) Field of Classification Search
None
See application file for complete search history.

(56) References Cited

U.S. PATENT DOCUMENTS

| | | | |
|---|---|---|---|
| 3,840,490 | A | 10/1974 | Gadzala |
| 4,384,058 | A | 5/1983 | Galante |
| 4,646,765 | A | 3/1987 | Cooper |
| 5,866,106 | A | 2/1999 | Papay |
| 6,086,906 | A | 7/2000 | Greff |
| 6,703,003 | B1 | 3/2004 | Kishita |
| 7,618,618 | B2 | 11/2009 | Lupia |
| 8,147,814 | B2 | 4/2012 | Song et al. |

*Primary Examiner* — Scott Long
*Assistant Examiner* — Sarah Alawadi
(74) *Attorney, Agent, or Firm* — Eric Karich

(57) ABSTRACT

A nail enamel composition has a film-forming mixture in a compatible solvent. The film-forming mixture includes nitrocellulose as a major component. The composition further includes a cyanoacrylate mixture comprising cyanoacrylate and a free radical inhibitor, the cyanoacrylate mixture being substantially free of toluene. The invention includes a method of preparation of the composition, and a method of use of the composition.

6 Claims, 1 Drawing Sheet

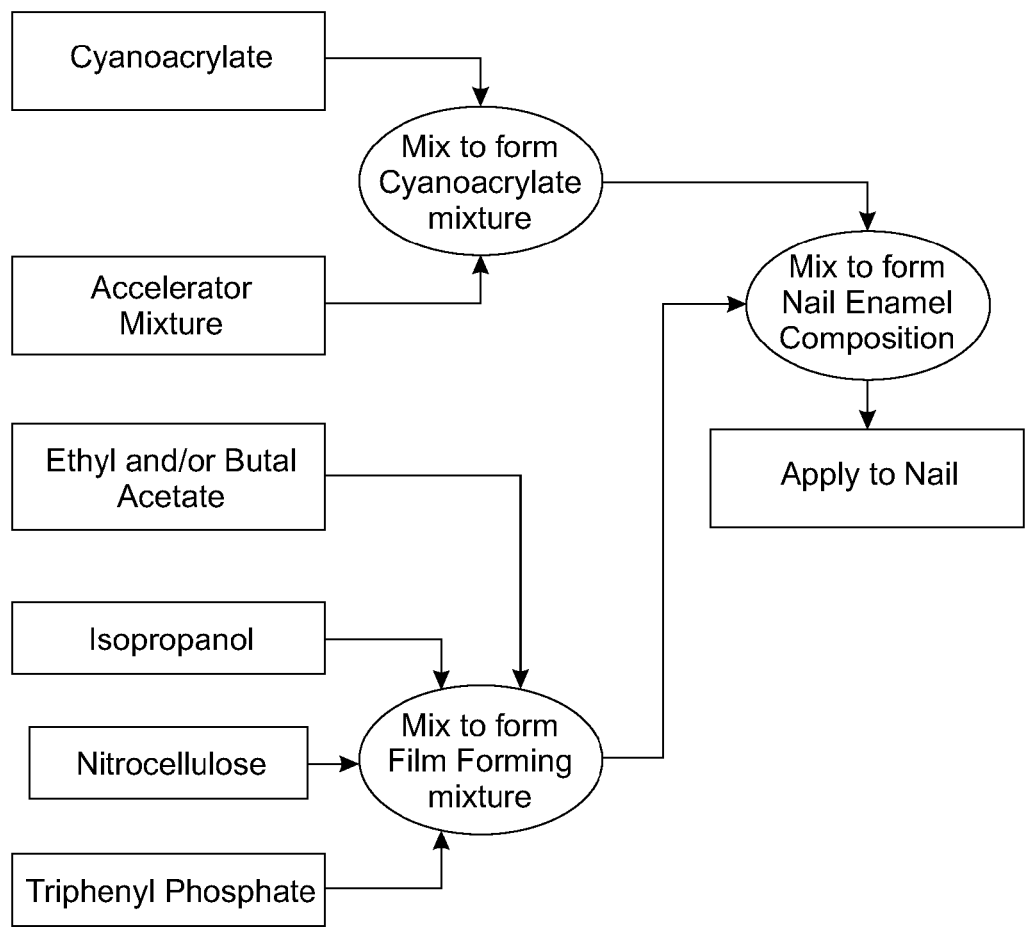

NAIL ENAMEL COMPOSITION, METHOD OF PREPARATION AND METHOD OF USE

CROSS-REFERENCE TO RELATED APPLICATIONS

This application for a utility patent is a divisional of a previously filed utility patent, still pending, having the application Ser. No. 13/633,436, filed Oct. 2, 2012.

STATEMENT REGARDING FEDERALLY SPONSORED RESEARCH

Not Applicable

BACKGROUND OF THE INVENTION

1. Field of the Invention

This invention relates generally to nail enamels, and more particularly to a nail enamel composition that includes cyanoacrylate and other components to provide improved durability, longevity, and scratch resistance, and faster drying times.

2. Description of Related Art

For purposes of this application, the term "nail enamel" is hereby defined to include any form of film-forming composition such as enamels, lacquers, top coats, base coats, and similar or equivalent materials that are used to coat a nail, whether clear or pigmented. For purposes of this application, the term "nail" is hereby defined to include natural fingernails, toenails, as well as artificial nails, nail tops, or plastic nails.

Conventional nail enamel products (i.e., nail polish) typically contain nitrocellulose as the main film-forming resin, and may further include additional resins, plasticizers, and other agents. Such products typically also include pigments, and a thixotropic agent for suspending the pigment, as well solvents such as n-butyl acetate, ethyl acetate, and toluene.

Galante, U.S. Pat. No. 4,384,058, teaches such an nail enamel, and further teaches the inclusion of an auxiliary resin to strengthen the enamel, preferably a film-forming styrene-acrylonitrile-acrylic terpolymer; however, a film-forming alkyl cyanoacrylate is also listed as an option for strengthening the enamel. Such cyanoacrylate additives typically include toluene, which is a disadvantage due to the offensive odor. Furthermore, it is noted in the discussion that their formulation does not provide a suitable gloss.

SUMMARY OF THE INVENTION

The present invention teaches certain benefits in construction and use which give rise to the objectives described below.

The present invention provides a nail enamel composition comprising a film-forming mixture comprising nitrocellulose as a major component; a compatible solvent; and a cyanoacrylate mixture comprising cyanoacrylate and a free radical inhibitor, the cyanoacrylate mixture being substantially free of toluene.

A primary objective of the present invention is to provide a nail enamel composition having advantages not taught by the prior art.

Another objective is to provide a nail enamel composition that provides improved resistance to wear and chipping Another objective is to provide a nail enamel composition that dries more quickly.

A further objective is to provide method of preparing and mixing the nail enamel composition to provide improved shelf life.

A further objective is to provide method of applying the nail enamel composition to provide improved strength and also an improved shine.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawing illustrates the present invention. In such drawing:

FIG. 1 is a flow diagram illustrating a method of preparation of a nail enamel composition according to one embodiment of the present invention.

DETAILED DESCRIPTION OF THE INVENTION

The above-described drawing figures illustrate the invention, a nail enamel composition and a method of preparing the nail enamel composition for use on a nail of a user.

The nail enamel composition comprises a film-forming mixture adapted for application to a human nail, and a cyanoacrylate mixture. The method of mixing the nail enamel composition is discussed in greater detail below.

The film-forming mixture includes nitrocellulose as a major component, and a compatible solvent. As discussed in greater detail below, the film-forming mixture may include nitrocellulose, ethyl and/or butyl acetate, isopropanol, and a free radical inhibitor. In one embodiment, the film-forming mixture includes triphenyl phosphate, and may further include additional chemicals, as discussed in greater detail below.

The cyanoacrylate mixture comprises cyanoacrylate and an accelerator mixture, and may further include a free radical inhibitor that does not include toluene, such as butylated hydroxyanisole The accelerator mixture may include acetone and ethyl acetate, as discussed in greater detail below. It is critical that the cyanoacrylate first be mixed with the accelerator mixture, as discussed below, prior to its addition to the film-forming mixture, to prevent crystallization of the mixture.

The film-forming mixture may comprise nitrocellulose as a major component, and may include any of the number of additives typically found in nail enamel (i.e., nail polish). In an alternative embodiment, the film-forming mixture may comprise a top coat, or similar coating applied on top of the nail enamel. In some embodiments, the film-forming mixture may include color pigment, and/or any form of texturing or decorative colors or features known in the art.

In one embodiment, the cyanoacrylate is 2-Ethyl cyanoacrylate. In this embodiment, the free radical inhibitor may be butylated hydroxyanisole. The solvent may be ethyl acetate and/or butyl acetate, and/or other acceptable solvents known in the art. In one embodiment, the cyanoacrylate mixture is substantially free of toluene. For purposes of this application, the term "substantially free of toluene" is defined to mean either no toluene at all, or such small traces of toluene that it does not cause any negative side effects such as irritation of the skin, noxious smell, or any other negative effects of toluene.

In one embodiment, the nail enamel composition comprises the following:

45-67% ethyl acetate and/or butyl acetate;
9-19% isopropanol;
9-28% nitrocellulose;
1-9% triphenyl phosphate;
0.01-1% diacetone alcohol;
0.01-0.2% butylated hydroxyanisole;
an operative amount of cyanoacrylate for substantially speeding the drying of the nail enamel composition, not exceeding 1% of the total weight of the nail enamel composition. Each percentage is a percentage by weight.

In one embodiment, the nail enamel composition comprises 27-37% ethyl acetate and 18-28% butyl acetate. In one embodiment, the nail enamel composition comprises 0.05-1% cyanoacrylate.

FIG. 1 is a flow diagram illustrating a method of preparing the nail enamel composition according to one embodiment of the present invention. As illustrated in FIG. 1, the method for forming the nail enamel composition comprises the steps of first mixing the cyanoacrylate with the accelerator mixture, to form the cyanoacrylate mixture. It is critical that the cyanoacrylate first be mixed with the accelerator mixture, as illustrated, to prevent crystallizing of the nail enamel composition. The cyanoacrylate mixture may further include a free radical inhibitor, in this case butylated hydroxyanisole, to form a cyanoacrylate mixture. In one embodiment, 0.01-3% of the cyanoacrylate mixture is the cyanoacrylate, once mixed with the accelerator mixture. In another embodiment, 0.1-5% of the cyanoacrylate mixture is the cyanoacrylate, once mixed with the accelerator mixture. In yet another embodiment, the cyanoacrylate mixture includes about 1% cyanoacrylate (about being defined to mean+/−10 percent). The cyanoacrylate mixture may further include less than 0.15% of the butylated hydroxyanisole, such as approximately 0.1% of the butylated hydroxyanisole.

The accelerator mixture may include 50-70% acetone and 30-50% ethyl acetate. Obviously, those skilled in the art may devise alternative formulations, and may add additional chemicals that don't interfere with the function of the accelerator mixture, and such alternative formulations should be considered within the scope of the present invention.

Separately, the nitrocellulose mixture is formed by mixing a film-forming mixture comprising nitrocellulose as a major component, with a compatible solvent to form the nitrocellulose mixture. The nitrocellulose mixture is then mixed with the cyanoacrylate mixture to form the nail enamel composition that is substantially free of toluene.

Keeping the cyanoacrylate, mixed with the free radical inhibitor, separate from the film-forming mixture extends the shelf life of the cyanoacrylate, so it is helpful to maintain the cyanoacrylate mixture separately from the film-forming mixture until they are ready to be mixed, packaged, and sold.

While FIG. 1 illustrates one embodiment of how the composition may be formed, those skilled in the art may devise alternative embodiments, and these alternative or equivalent are considered within the scope of the present invention.

The invention further includes a method of applying the nail enamel composition to a nail of a person or animal. In a first embodiment, a first layer of a nail bonding/preparation solution is applied. The nail bonding/preparation solution may include a primer, a bonding agent, and/or any other form of preparation solution known in the art. In another embodiment, however, this step may be omitted, depending upon the needs of the user.

A coat of nail base may then be provided. The nail base provides a protective layer that maximizes color adhesion and eliminates staining. The nail base may comprise, in one embodiment, isopropyl alcohol, ethyl and butyl acetate, polyvinyl butyral, nitrocellulose, trimethyl pentanyl diisobutyrate, tosylamide formaldehyde resin, and benzophenone. In other embodiments, other known nail base formulations may be used.

One or more coats of the nail enamel composition are then applied, depending upon how dark the color is desired. Since the application of the nail enamel composition is well known in the art, and is described in greater detail above, further discussion of this step is not required.

Finally, a top coat may be applied. The top coat provides a glossy finish and may also include a wide range of special effects. The top coat may comprise standard ingredients, such as nitrocellulose, ethyl an butyl acetate, cellulose acetate butyrate, n-butyl alcohol, propyl acetate, trimethyl pentanyl diisobutyrate, phthalic anhydride/trimellitic anhydride/glycols copolymer, acrylates copolymer, acrylates copolymer, bis-phenylpropyl dimethicone, etocrylene, and isopropyl alcohol. These ingredients may be modified or substituted according to the requirements of one skilled in the art, and such alternatives should be considered within the scope of the present invention.

In another embodiment, the top coat may include various natural extracts, such as *chamomilla recutita* (matricaria) extract, *citrus aurantium dulcis* (orange) flower water, hydrolyzed conchiolin protein, *lilium candidum* bulb extract, retinyl palmitate, *simmondsia chinensis* (jojoba) seed oil, tocopherol, *arachis hypogaea* (peanut) oil, benzyl benzoate, butylene glycol, as well as acetyl tributyl citrate, sucrose benzoate, isopropyl alcohol, methylparaben, alpha-isomethylionone, and butylphenyl methylpropional.

As used in this application, the words "a," "an," and "one" are defined to include one or more of the referenced item unless specifically stated otherwise. Also, the terms "have," "include," "contain," and similar terms are defined to mean "comprising" unless specifically stated otherwise. Furthermore, the terminology used in the specification provided above is hereby defined to include similar and/or equivalent terms, and/or alternative embodiments that would be considered obvious to one skilled in the art given the teachings of the present patent application.

What is claimed is:

1. A method for forming a nail enamel composition, the method comprising the steps of:
   first, mixing a cyanoacrylate with an accelerator mixture to form a cyanoacrylate mixture, wherein the cyanoacrylate is less than 5% of the cyanoacrylate mixture;
   mixing a film-forming mixture comprising nitrocellulose and a compatible solvent to form a nitrocellulose mixture; and
   then, mixing the cyanoacrylate mixture and the nitrocellulose mixture to form the nail enamel composition.

2. The method of claim 1 further comprising the step of applying the nail enamel composition to a nail of a person or animal.

3. The method of claim 1, wherein the film-forming mixture further comprises a color pigment.

4. The method of claim 1, wherein the nail enamel composition is substantially free of toluene.

5. The method of claim 1, wherein the cyanoacrylate mixture includes about 1% cyanoacrylate.

6. The method of claim 1, wherein the cyanoacrylate mixture includes between 0.01-3% cyanoacrylate.

* * * * *